(12) United States Patent
Huang et al.

(10) Patent No.: US 11,801,145 B2
(45) Date of Patent: Oct. 31, 2023

(54) TEMPOROMANDIBULAR JOINT PROSTHESIS

(71) Applicant: INDUSTRIAL TECHNOLOGY RESEARCH INSTITUTE, Hsinchu (TW)

(72) Inventors: Wei-Chin Huang, Tainan (TW); Sung-Ho Liu, Kaohsiung (TW); Chuan-Sheng Chuang, Tainan (TW); An-Li Chen, Tainan (TW); Chun-Feng Chen, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 267 days.

(21) Appl. No.: 17/199,096

(22) Filed: Mar. 11, 2021

(65) Prior Publication Data

US 2022/0133482 A1 May 5, 2022

(30) Foreign Application Priority Data

Nov. 4, 2020 (TW) .................. 109138334

(51) Int. Cl.
*A61F 2/30* (2006.01)

(52) U.S. Cl.
CPC .. *A61F 2/3099* (2013.01); *A61F 2002/30985* (2013.01); *A61F 2310/00017* (2013.01); *A61F 2310/00023* (2013.01); *A61F 2310/00029* (2013.01); *A61F 2310/00179* (2013.01)

(58) Field of Classification Search
CPC .......... A61F 2/3099; A61F 2002/30985; A61F 2310/00017; A61F 2310/00023; A61F 2310/00029; A61F 2310/00179
See application file for complete search history.

(56) References Cited

U.S. PATENT DOCUMENTS

| | | | |
|---|---|---|---|
| 3,178,728 A | 4/1965 | Christensen |
| 3,707,006 A | 12/1972 | Bokros et al. |
| 3,720,959 A | 3/1973 | Hahn |
| 4,778,472 A | 10/1988 | Homsy et al. |

(Continued)

FOREIGN PATENT DOCUMENTS

| | | |
|---|---|---|
| CN | 204766045 U | 11/2015 |
| CN | 210749670 U | 6/2020 |

(Continued)

OTHER PUBLICATIONS

Taiwan Office Action dated Jul. 14, 2021 as received in application No. 109138334.

(Continued)

*Primary Examiner* — Keri J Nelson
*Assistant Examiner* — Rebecca Lynee Zimmerman
(74) *Attorney, Agent, or Firm* — Maschoff Brennan

(57) ABSTRACT

The disclosed embodiments relate to a temporomandibular joint prosthesis including a joint portion, a fixation portion, and at least one flexible unit. The joint portion is configured to be as a temporomandibular joint and movably connected to cranial skeleton. The fixation portion is configured to be fixed on mandible. The flexible unit is located between and connected to the joint portion and the fixation portion. The fixation portion is movable with respect to the joint portion via the flexible unit.

6 Claims, 13 Drawing Sheets

(56) References Cited

U.S. PATENT DOCUMENTS

| | | | |
|---|---|---|---|
| 4,917,701 | A | 4/1990 | Morgan et al. |
| 4,936,852 | A | 6/1990 | Kent et al. |
| 5,405,393 | A | 4/1995 | Falkenstroem et al. |
| 5,445,650 | A | 8/1995 | Nealis |
| 5,549,680 | A | 8/1996 | Gordon |
| 6,132,466 | A | 10/2000 | Hoffman et al. |
| 9,517,135 | B2 | 12/2016 | Ramos et al. |
| 2010/0057209 | A1 | 3/2010 | Keller et al. |
| 2016/0081806 | A1* | 3/2016 | Dubois ............... A61F 2/4603 623/17.17 |
| 2019/0192302 | A1 | 6/2019 | Mommaerts et al. |
| 2020/0093602 | A1 | 1/2020 | Taylor |

FOREIGN PATENT DOCUMENTS

| | | |
|---|---|---|
| WO | 2014/043452 A1 | 3/2014 |
| WO | 2016/014006 A1 | 1/2016 |
| WO | 2017/075664 A1 | 5/2017 |

OTHER PUBLICATIONS

Hussain, et al., "Prospective comparison study of one-year outcomes for all titanium total temporomandibular joint replacements in patients allergic to metal and cobalt-chromium replacement joints in patients not allergic to metal," Elsevier, pp. 34-37 (Feb. 4, 2013).

Ackland, et al., "A personalized 3D-printed prosthetic joint replacement for the human temporomandibular joint: From implant design to implantation," Journal of the Mechanical Behavior of Biomedical Materials, Issue 69, pp. 404-411 (Feb. 6, 2017).

Ackland, et al., "Design and clinical outcome of a novel 3D-printed prosthetic joint replacement for the human temporomandibular joint," Accepted Manuscript, pp. 1-36 (May 8, 2018).

Chen, et al., "Biomechanical evaluation of Chinese customized three-dimensionally printed total temporomandibular joint prostheses: A finite element analysis," Accepted Manuscript, pp. 1-42 (Jun. 28, 2018).

Zheng, et al., "An innovative total temporomandibular joint prosthesis with customized design and 3D printing additive fabrication: a prospective clinical study," Journal of Translational Medicine, pp. 1-10 (2019).

Zheng, et al., "Customized skull base-temporomandibular joint combined prosthesis with 3D-printing fabrication for craniomaxillofacial reconstruction: a preliminary study," Clinical PaperTMJ Disorders, pp. 1440-1447 (Mar. 21, 2019).

Yoda, et al., "Clinical guidelines for total temporomandibular joint replacement," Japanese Dental Science Review, pp. 77-83 (Mar. 1, 2020).

* cited by examiner

TEMPOROMANDIBULAR JOINT PROSTHESIS

CROSS-REFERENCE TO RELATED APPLICATIONS

This non-provisional application claims priority under 35 U.S.C. § 119(a) on Patent Application No(s). 109138334 filed in Taiwan (R.O.C.) on Nov. 4, 2020, the entire contents of which are hereby incorporated by reference.

TECHNICAL FIELD

The disclosure relates to an implant, more particularly to a temporomandibular joint prosthesis.

BACKGROUND

In recent years, the incidence of oral, oropharyngeal and hypopharyngeal malignant tumors largely increases. According to official statistics in Taiwan in 2016, there are about 7,897 people who preliminary diagnosed with oral, oropharyngeal and hypopharyngeal malignant tumors, and the majority of these cases (around 64.96%) took surgical procedure to remove the tumor since it is considered the most reliable treatment.

Taking the mandible as an example, the mandible is the support and lowest bone in the human facial skeleton to form the lower jaw and hold the lower teeth in place, there are temporomandibular joints (TMJ) being bilateral synovial articulation between the temporal bone of the skull and the mandible, it is found that a high proportion of patients with mandible tumor is caused by temporomandibular joint disease, and around 30% of them need to take mandibulectomy to remove all or part of mandible.

The resection of the tumor and all or part of the mandible leave a cavity that is likely to cause poor wound healing, affecting chewing, swallowing, and speaking functions, and also to result in seriously changes to the appearance of the face. Thus, reconstruction will be needed to help maintain patient's jaw function and fairly normal outward appearance. The conventional reconstruction following segmental mandibulectomy is vascularized autologous bone graft in the form of the fibula flap. However, in bone reconstruction the use of autogenous bone does not always guarantee a successful outcome since it is difficult to shape the autologous fibula flap to match the contour of the removal parts, still failing to maintain the jaw's functions and outward appearance.

In this concern, 3D printed models begin to be used in mandibular reconstruction, making it possible to customize temporomandibular joint implant suitable for each patient. However, the existing artificial temporomandibular joint implants do not have a flexibility able to respond to the complex three-dimensional movement during the activities, such as speaking, chewing, and swallowing, thus resulting in stress concentration on parts of the boundaries. The stress concentration may cause pain, muscle tenderness and uncomfortable sensation. According to statistics, at least 80% of those who use artificial temporomandibular joint suffer from above discomfort caused by stress concentration and have higher risk in causing damage to their implants.

SUMMARY

Accordingly, the present disclosure provides a temporomandibular joint prosthesis that is capable of effectively reducing or even avoiding the stress concentration.

One embodiment of the disclosure provides a temporomandibular joint prosthesis including a joint portion, a fixation portion, and at least one flexible unit. The joint portion is configured to be as a temporomandibular joint and movably connected to cranial skeleton. The fixation portion is configured to be fixed on mandible. The flexible unit is located between and connected to the joint portion and the fixation portion. The fixation portion is movable with respect to the joint portion via the flexible unit.

According to the temporomandibular joint prosthesis as discussed in the above embodiments of the disclosure, during the various activities, such as speaking, chewing, and swallowing, the flexible unit connected between the joint portion and the fixation portion enables complex three-dimensional movements of the temporomandibular joint prosthesis and at the same time can be served as a cushion to reduce or remove stress concentration. As a result, the patient who used this temporomandibular joint prosthesis is free from pain, muscle tenderness, and uncomfortable sensation during the movement of lower jaw. In addition, the cushion provided by the flexible unit helps increase the durability and lifespan of the temporomandibular joint prosthesis.

BRIEF DESCRIPTION OF THE DRAWINGS

The present disclosure will become better understood from the detailed description given hereinbelow and the accompanying drawings which are given by way of illustration only and thus are not intending to limit the present disclosure and wherein.

DETAILED DESCRIPTION

Figure 1:
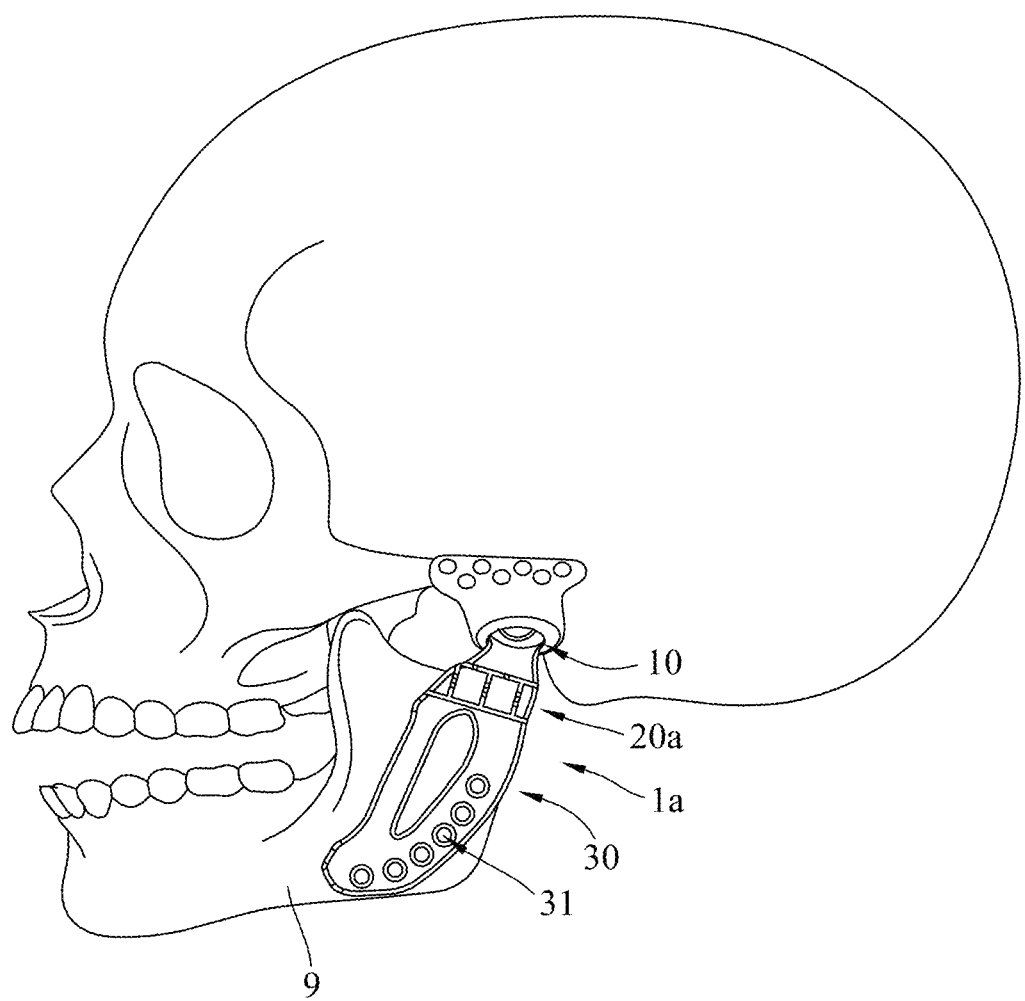
FIG. 1 is a perspective view of a temporomandibular joint prosthesis being implanted in skeleton according to one embodiment of the disclosure.

In the following detailed description, for purposes of explanation, numerous specific details are set forth in order to provide a thorough understanding of the disclosed embodiments. It will be apparent, however, that one or more embodiments may be practiced without these specific details.

The following embodiments will be described with reference to the drawings. For the purpose of clear illustration, some conventional elements and components may be illustrated in a simple and clear manner. Some of the features in the drawings may be slightly exaggerated or illustrated in a larger proportion for the ease of viewing but are not intended to limit the disclosure. In addition, for the same reason, some of the elements or components in the drawings may be illustrated in dotted lines.

Herein, the terms, such as "end", "part", "portion", "area", may be used to refer to specific features of or between elements or components but are not intended to limit the elements and components. In addition, the terms, such as "substantially" and "approximately", as used herein may mean a reasonable amount of deviation of the described term such that the end result is not significantly changed.

Further, unless explicitly stated, the term "at least one" as used herein may mean that the quantity of the described element or component is one or larger than one but does not necessarily mean that the quantity is only one. The term "and/or" may be used herein to indicate that either or both of two stated possibilities.

Figure 2A:
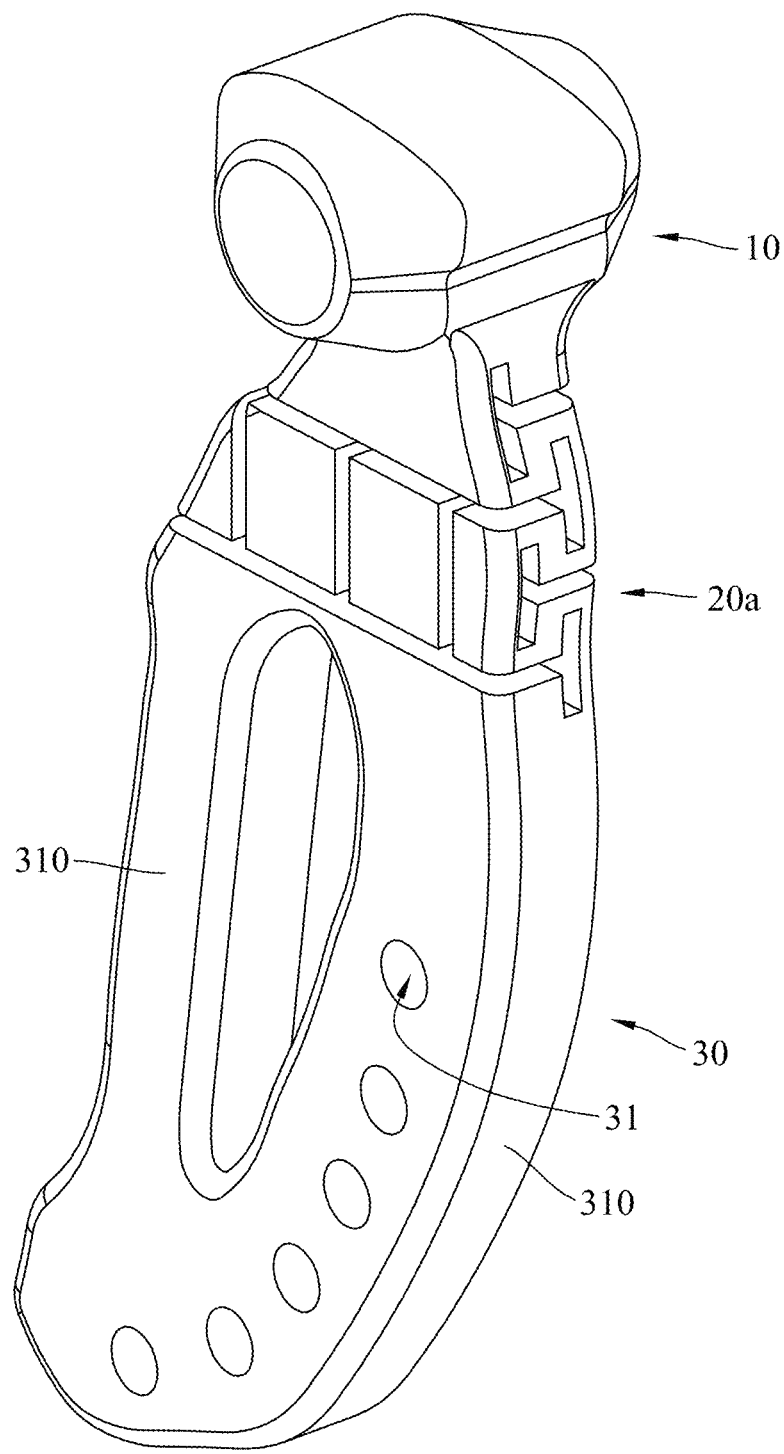
FIGS. 2A-2C illustrate different perspective views of the temporomandibular joint prosthesis in FIG. 1.
Figure 2B:
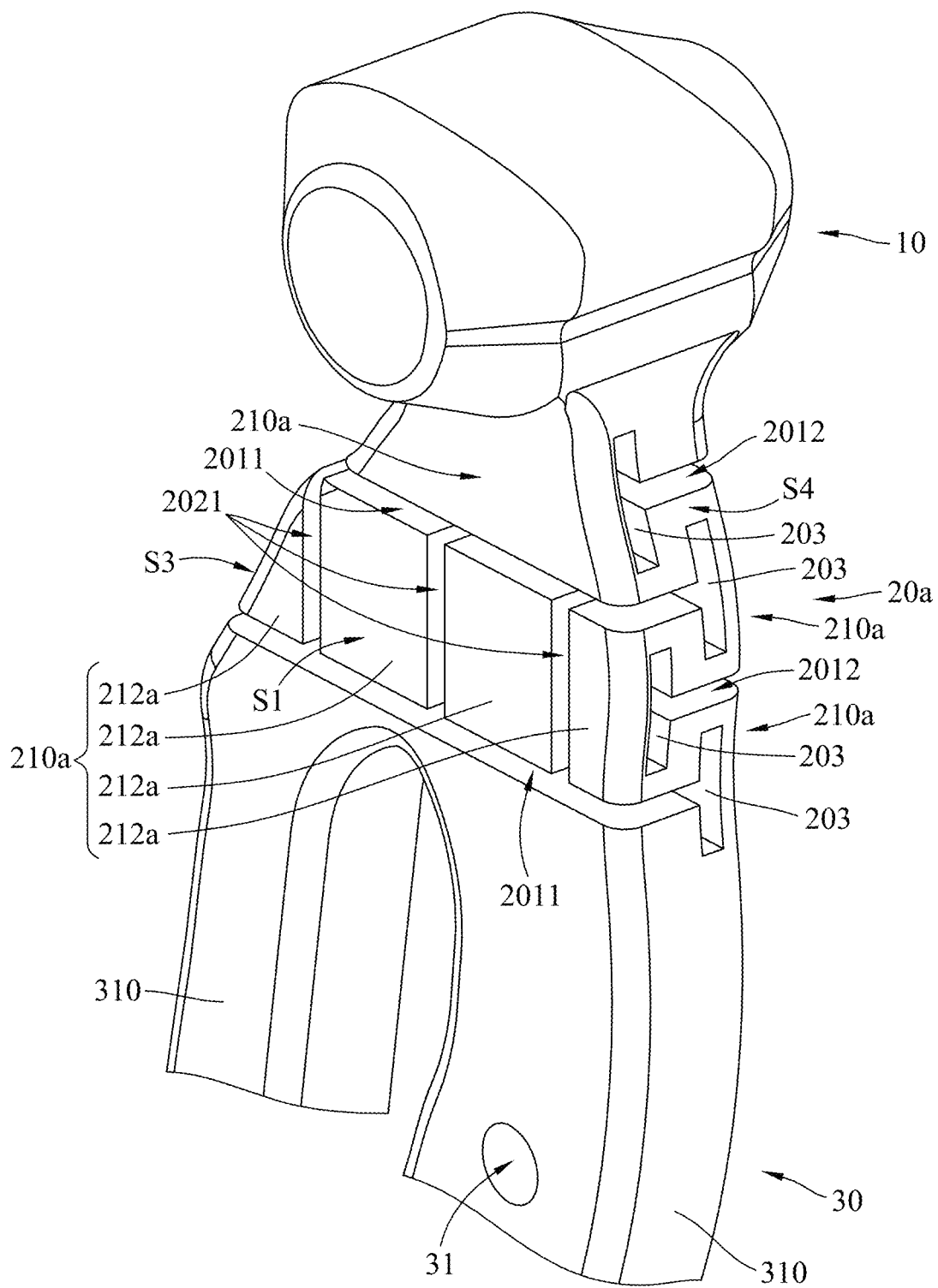
Figure 2C:
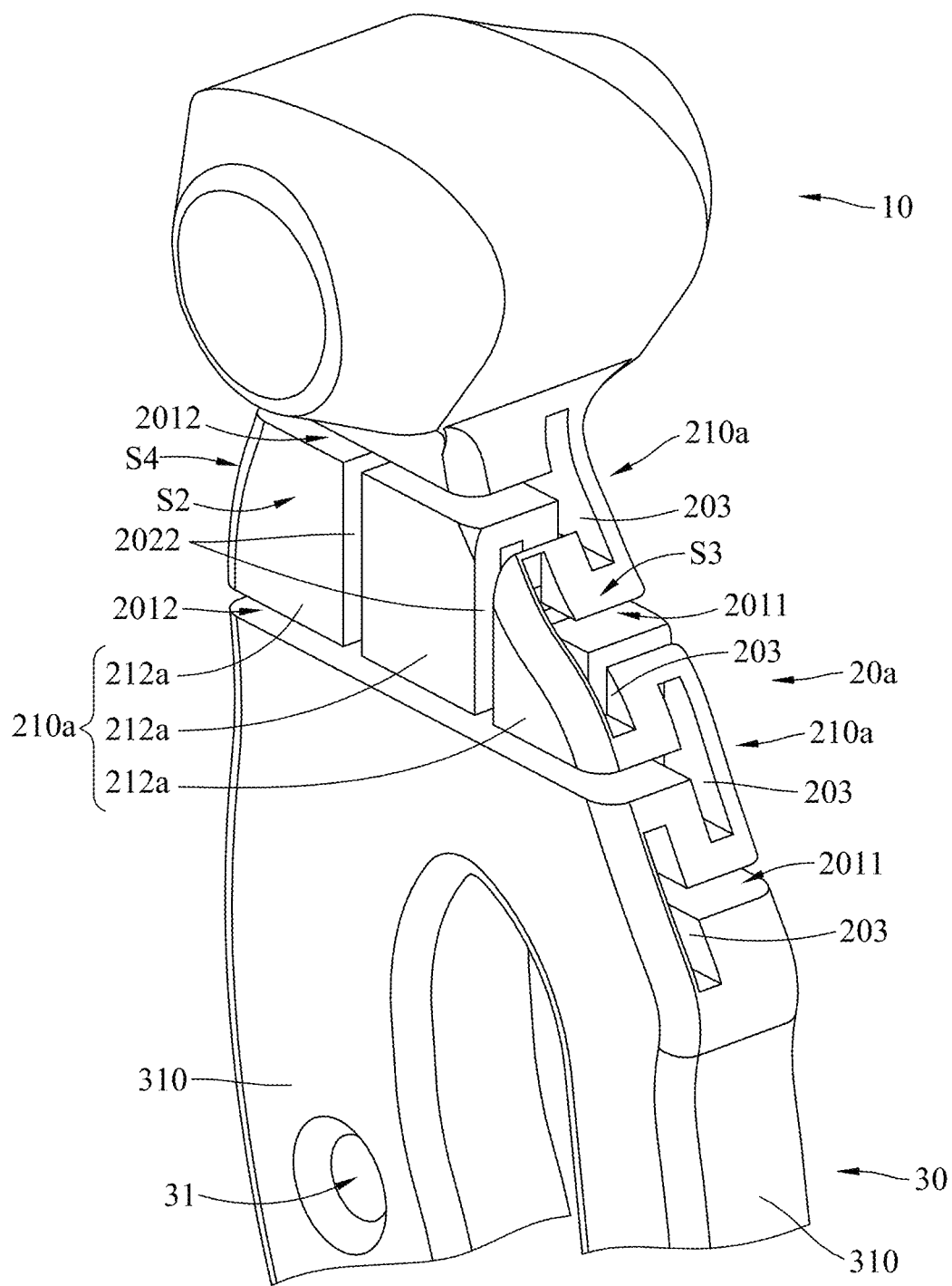

The temporomandibular joint prosthesis provided by the embodiments of the disclosure are suitable for reconstruction following mandibulectomy. Firstly, referring to FIGS. 1-2B, one of embodiments of the disclosure provides a temporomandibular joint prosthesis 1a, as shown, the temporomandibular joint prosthesis 1a is implanted in a mandible 9, where the mandible 9 is illustrated for exemplary purpose. It is noted that the temporomandibular joint prosthesis 1a not only can maintain the jaw's functions and outward appearance but also can enable complex three-dimensional movements of the temporomandibular joint prosthesis while serving as a cushion to reduce or remove stress concentration, thereby avoiding discomforts caused by stress concentration. The detail descriptions are given below.

In this embodiment, the temporomandibular joint prosthesis 1a is integrally 3D-printed using biocompatible material, such as titanium alloy, iron-based alloy, cobalt alloy, polymer material, ceramic, a combination thereof, but the materials of the temporomandibular joint prosthesis 1a is selective as required. It is noted that the 3D printing technology avoid using the vascularized autologous bone graft and makes the temporomandibular joint prosthesis 1a perfectly match the contour of the removal parts and maximally restore the normal outward appearance of the patient. It is also noted that the 3D printing technology can render solid or porous material for the temporomandibular joint prosthesis 1a.

Further, the structural details of the temporomandibular joint prosthesis 1a are illustrated hereinafter. In this embodiment, the temporomandibular joint prosthesis 1a may include a joint portion 10, at least one flexible unit 20a, and a fixation portion 30. The joint portion 10 is arranged at an end of the temporomandibular joint prosthesis 1a, the joint portion 10 has a shape of a sphere or ball and is movably connected to cranial skeleton so as to be served as a replacement of a temporomandibular joint (TMJ). In more detail, as shown, the joint portion 10 may be connected to the cranial skeleton via a suitable temporal prosthesis (not numbered), but the disclosure is not limited by the temporal prosthesis cooperated with the temporomandibular joint prosthesis 1a and its design. It should be noted that the joint portion 10 can be shaped or sized as required as long as it help improve the reconstruction.

The fixation portion 30 is the part of the temporomandibular joint prosthesis 1a to be embedded into or directly fixed to the mandible 9. The fixation portion 30 has one or more bone screw holes 31 penetrating through a first surface S1 and a second surface S2 of the temporomandibular joint prosthesis 1a. The bone screw hole 31 is for the insertion of a suitable bone screw into the mandible 9, such that the fixation portion 30 can be fixed to the mandible 9.

Further, the fixation portion 30 may include two support portions 310 connected to each other at opposite ends, the support portions 310 leave a space therebetween so that the fixation portion 30 is light while having an improved structural strength.

It should be noted that the fixation portion 30 can be shaped or sized as required as long as it can be secured in place. For example, in other embodiments, the fixation portion may only have one support portion or may have a plate-like shape.

The flexible unit 20a is the part of the temporomandibular joint prosthesis 1a connected between the fixation portion 30 and the joint portion 10. The flexible unit 20a enables complex three-dimensional movements of the temporomandibular joint prosthesis 1a in response to the activities, such as speaking, chewing, and swallowing, while avoiding resulting in stress concentration. As shown, except for the joint portion 10, the rest parts of the temporomandibular joint prosthesis 1a are in a shape of flat plate, in such a case, the first surface S1, the second surface S2, a third surface S3, and a fourth surface S4 are given to indicate the surfaces at four different sides of the plate shape of the temporomandibular joint prosthesis 1a, where the first surface S1 and the second surface S2 are located opposite each other and indicate two relatively flat and large areas of the plate shape, and the third surface S3 and the fourth surface S4 are located opposite each other and located between the first surface S1 and the second surface S2 and indicate two smaller areas at the edges between the first surface S1 and the second surface S2. The detail of the flexible unit in this or other embodiments will be described with reference to the first surface S1, the second surface S2, the third surface S3, and the fourth surface S4, thus, in the following paragraphs, the first surface S1, the second surface S2, the third surface S3, and the fourth surface S4 will be employed to indicate different surfaces of the flexible unit.

Generally, the flexible unit 20a of this embodiment may include a plurality of elastic portions 210a, each of the elastic portions 210a has a C-like shape, the elastic portions 210a are connected to end to end so as to form a serpentine shape. In addition, at least one or more of the elastic portions 210a include a plurality of elastic sub-units 212a spaced apart from one another. It is understood that the elastic sub-unit 212a is in C-like shape as well.

More specifically, the flexible unit 20a may have a plurality of first trenches 2011 (may simply be called 'trench 2011' hereinafter), a plurality of second trenches 2012 (may simply be called 'trench 2012' hereinafter), a plurality of third trenches 2021 (may simply be called 'trench 2021' hereinafter), a plurality of fourth trenches 2022 (may simply be called 'trench 2022' hereinafter), and a plurality of fifth trenches 203 (may simply be called 'trench 203' hereinafter). The trenches 203 penetrate the third surface S3 and the fourth surface S4, in other words, the trenches 203 extend from the third surface S3 to the fourth surface S4. In addition, a part of the trenches 203 are located closer to and arranged in a line along the first surface S1, and the another part of the trenches 203 are located closer to and arranged in another line along the second surface S2, and the trenches 203 in these two lines are not aligned with each other but have a partial overlapping. The trenches 2011 penetrate the third surface S3 and the fourth surface S4, in other words, the trenches 2011 extend from the third surface S3 to the fourth surface S4. In addition, the trenches 2011 extend to the tranches 203, that are located closer the second surface S2, from the first surface S1 towards the second surface S2. The trenches 2012 penetrate the third surface S3 and the fourth surface S4, in other words, the trenches 2012 extend from the third surface S3 to the fourth surface S4. In addition, the trench 2012 extend to the tranches 203, that are located closer the first surface S1, from the second surface S2 towards the first surface S1. Viewing from the third surface S3 or the fourth surface S4, the trenches 2011 and the trenches 2012 are arranged in an alternate manner.

The trenches 2021 are spaced apart from one another. The trenches 2021 extend from the first surface S1 towards the second surface S2 and penetrate through the trenches 203, that are located closer the first surface S1, but not yet reach or directly connect the trenches 203 that are located closer the second surface S2, where the trenches 2011 and the trenches 2021 on the first surface S1 extend in different directions (e.g., the trenches 2011 and the trenches 2021 are orthogonal to each other). In other words, the trenches 2021 extend from one trench 2011 to the other. The trenches 2022 are spaced apart from one another. The trenches 2022 extend from the second surface S2 towards the first surface S1 and penetrate through the trenches the trenches 203, that are located closer the second surface S2, but not yet or directly connect the trenches 203 that are located closer the first surface S1, where the trenches 2012 and the trenches 2022 on the second surface S2 extend in different directions (e.g., the trenches 2012 and the trenches 2022 are orthogonal to each other). In other words, the trenches 2022 extend from one trench 2022 to the other.

The above arrangement of trenches on the flexible unit 20a can enable complex three-dimensional motions of the fixation portion 30 and the joint portion 10 during the activities of lower jaw while making the flexible unit 20a a cushion to effectively reduce or remove stress concentration on the boundaries among the temporomandibular joint prosthesis 1a, the mandible 9, and/or the cranial skeleton, thereby maintaining the jaw's functions and outward appearance and preventing pain, muscle tenderness, and uncomfortable sensation. In addition, the cushion provided by the flexible unit 20a helps increase the durability and lifespan of the temporomandibular joint prosthesis 1a.

Figure 3:
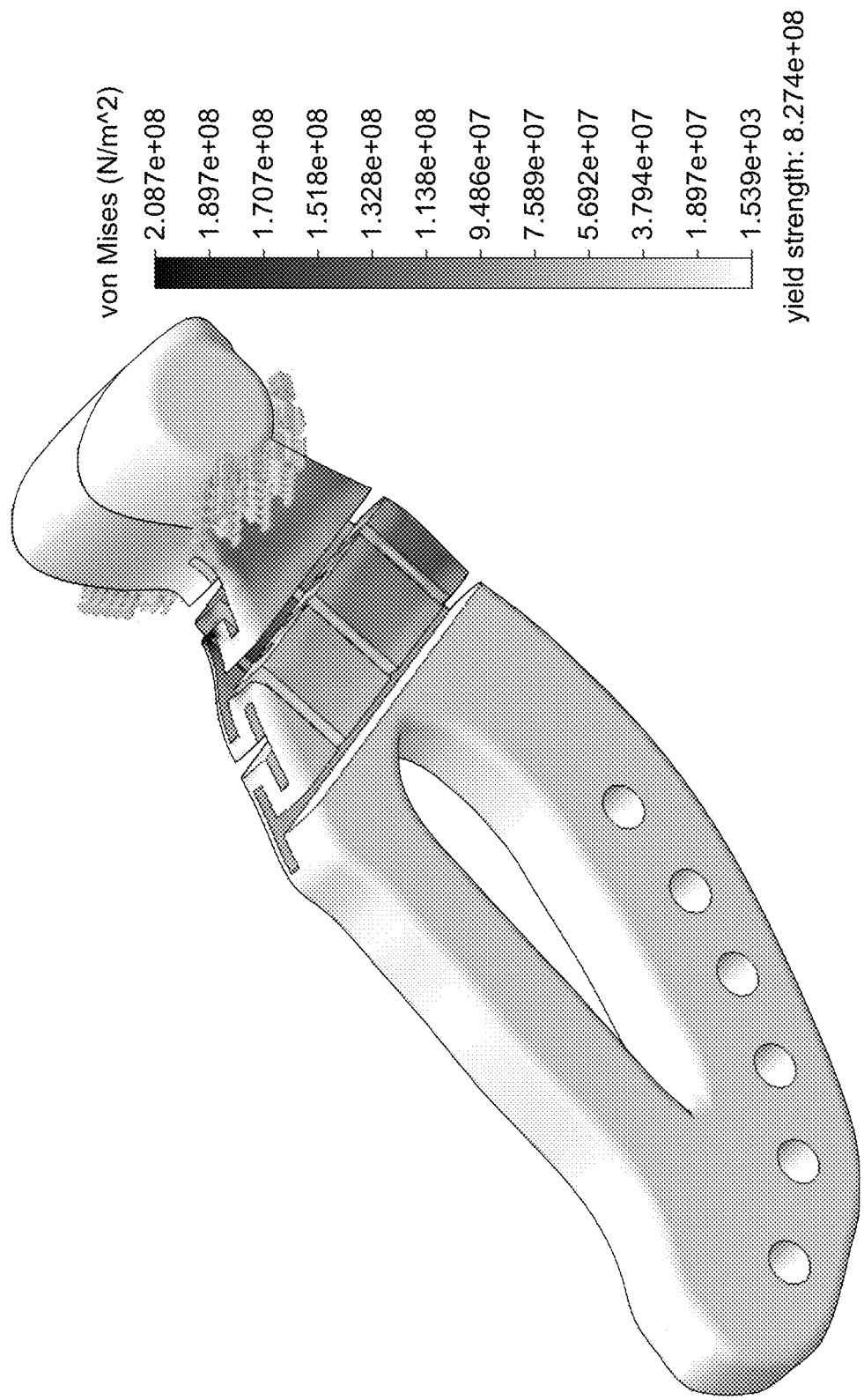
FIG. 3 is a stress concentration simulation of the temporomandibular joint prosthesis in FIG. 1.

Herein, referring to FIG. 3, there is shown a stress concentration simulation of the temporomandibular joint prosthesis 1a. Normally, high stress concentration is often found in or near the joint portion of the conventional temporomandibular joint prosthesis, but as can be seen in the simulation, the joint portion 10 and its part being connected to the flexible unit 20a is not found any high stress concentration distribution, the highest value in the said area is merely $2.37*10^8$ N/m$^2$. Compared with the statistics of the conventional temporomandibular joint prosthesis, the temporomandibular joint prosthesis 1a at least has a reduction of 80% of stress concentration and thus having significantly improvement in cushioning capability, durability, and lifespan.

It is noted that the above temporomandibular joint prosthesis is exemplary and not intended to limit the disclosure. Also, the sizes, shapes, quantities, and arrangements of the elastic portions and trenches in the flexible unit may be modified as required.

In this regard, various temporomandibular joint prosthesis of other embodiments of the disclosure are given below. Note that except for the design of the flexible unit, the other part of the temporomandibular joint prosthesis in the following embodiments are the same or similar to that of the previous embodiment, thus only the difference not yet described will be provided in the following paragraphs and the same or similar parts among the embodiments will not be repeated.

Figure 4:
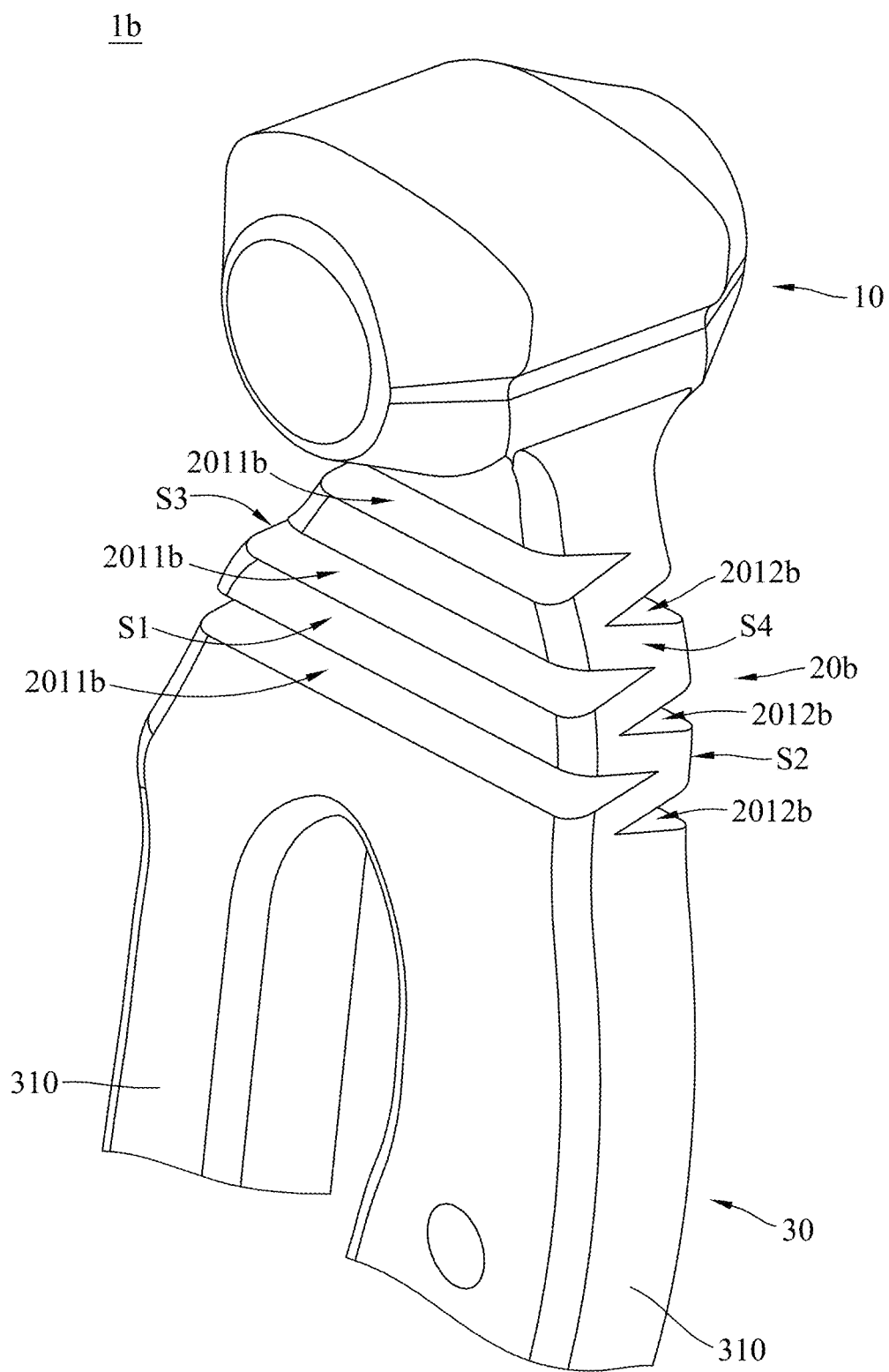
FIG. 4 illustrates a perspective view of a temporomandibular joint prosthesis according to another embodiment of the disclosure.

Referring to FIG. 4, another embodiment of the disclosure provides a temporomandibular joint prosthesis 1b, as shown, a flexible unit 20b forms a serpentine-shaped spring connected between the joint portion 10 and the fixation portion 30 and having trenches arranged in a staggered manner. In specific, the flexible unit 20b has a plurality of first trenches 2011b (may simply be called 'trench 2011b' hereinafter) and a plurality of second trenches 2012b (may simply be called 'trench 2012b' hereinafter). The trenches 2011b penetrate through the third surface S3 and the fourth surface S4, in other words, the trenches 2011b extend from the third surface S3 to the fourth surface S4. In addition, the trenches 2011b extend from the first surface S1 towards the second surface S2 but not yet reach or penetrate through the second surface S2. In this embodiment, each of the trenches 2011b is tapered towards the second surface S2 so that it is a triangle through hole penetrating through the third surface S3 and the fourth surface S4. The trenches 2012b penetrate through the third surface S3 and the fourth surface S4, in other words, the trenches 2012b extend from the third surface S3 to the fourth surface S4. In addition, the trenches 2012b extend from the second surface S2 towards the first surface S1 but not yet reach or penetrate through the first surface S1. In this embodiment, each of the trenches 2012b is tapered towards the first surface S1 so that it is a triangle through hole penetrating through the third surface S3 and the fourth surface S4. The trenches 2011b and the trenches 2012b are arranged in a staggered manner.

The flexible unit 20b also can enable complex three-dimensional motions of the fixation portion 30 and the joint portion 10 during the activities of lower jaw while serving as a cushion to effectively reduce or remove stress concentration on the boundaries among the temporomandibular joint prosthesis 1b, the mandible, and/or the cranial skeleton, thereby maintaining the jaw's functions and outward appearance and preventing pain, muscle tenderness, and uncomfortable sensation. For these reasons, the flexible unit 20b also helps increase the durability and lifespan of the temporomandibular joint prosthesis 1b.

Figure 5:
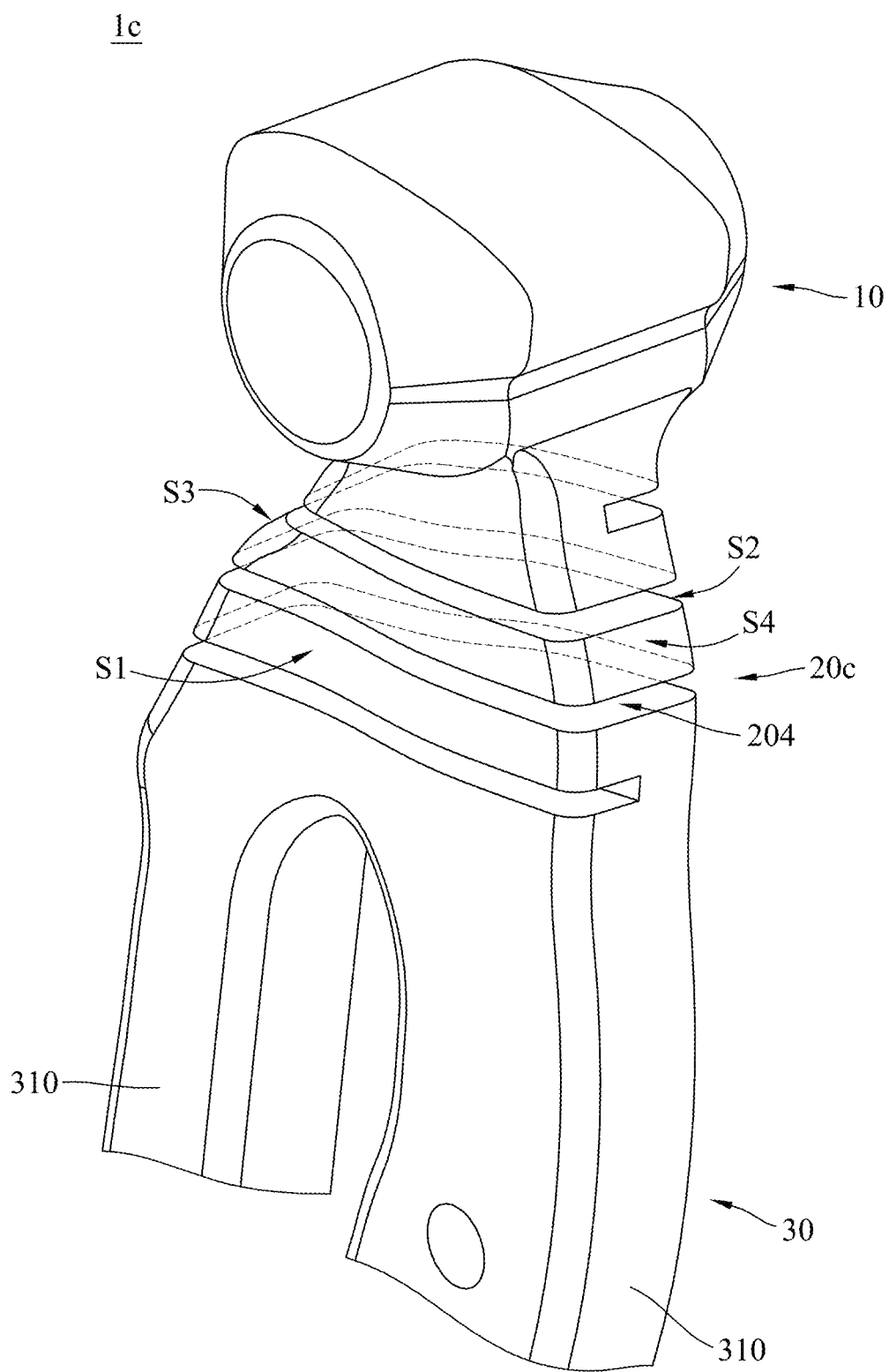
FIG. 5 illustrates a perspective view of a temporomandibular joint prosthesis according to another embodiment of the disclosure.

Alternatively, referring to FIG. 5, another embodiment of the disclosure provides a temporomandibular joint prosthesis 1c, as shown, a flexible unit 20c has a trench 204 in spiral shape so that it is a spiral-shaped spring connected between the joint portion 10 and the fixation portion 30. The shape of the flexible unit 20c also can enable complex three-dimensional motions of the fixation portion 30 and the joint portion 10 during the activities of lower jaw while serving as a cushion to effectively reduce or remove stress concentration on the boundaries among the temporomandibular joint prosthesis 1c, the mandible, and/or the cranial skeleton, thereby maintaining the jaw's functions and outward appearance and preventing pain, muscle tenderness, and uncomfortable sensation. For these reasons, the flexible unit 20c also helps increase the durability and lifespan of the temporomandibular joint prosthesis 1c.

Figure 6:
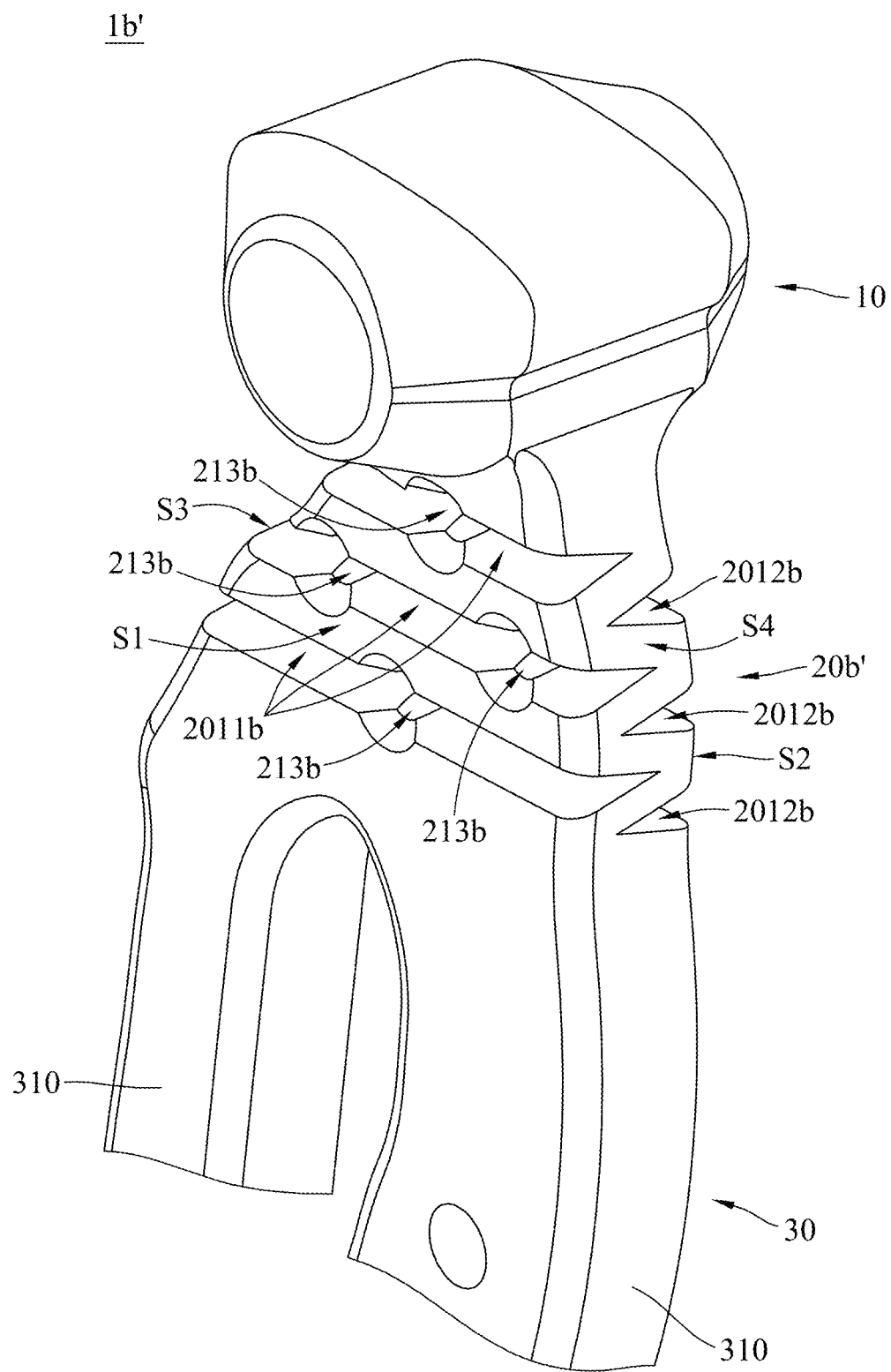
FIG. 6 illustrates a perspective view of a temporomandibular joint prosthesis according to another embodiment of the disclosure.

Alternatively, referring to FIG. 6, another embodiment of the disclosure provides a temporomandibular joint prosthesis 1b', as shown, having a configuration similar to that of the temporomandibular joint prosthesis 1b except for that a flexible unit 20b' of the temporomandibular joint prosthesis 1b' further has one or more adjustment holes 213b extending from the first surface S1 towards the second surface S2 and overlapping with one or more of the trenches 2011b. The adjustment holes 213b are formed for the insertion of suitable bone screw (not shown) so that the shapes of the trenches 2011b and 2012b can be adjusted by adjusting the insertion depth of the inserted bone screw, thereby adjusting the shape of the flexible unit 20b'. Other than that, the flexible unit 20b' still can enable complex three-dimensional motions of the fixation portion 30 and the joint portion 10 during the activities of lower jaw while serving as a cushion to effectively reduce or remove stress concentration on the boundaries among the temporomandibular joint prosthesis 1b', the mandible, and/or the cranial skeleton, thereby maintaining the jaw's functions and outward appearance and preventing pain, muscle tenderness, and uncomfortable sensation. For these reasons, the flexible unit 20b' also helps increase the durability and lifespan of the temporomandibular joint prosthesis 1b'. In other embodiments, the adjustment holes 213b may be formed on the second surface S2 and overlapping the trenches 2012b.

Figure 7:
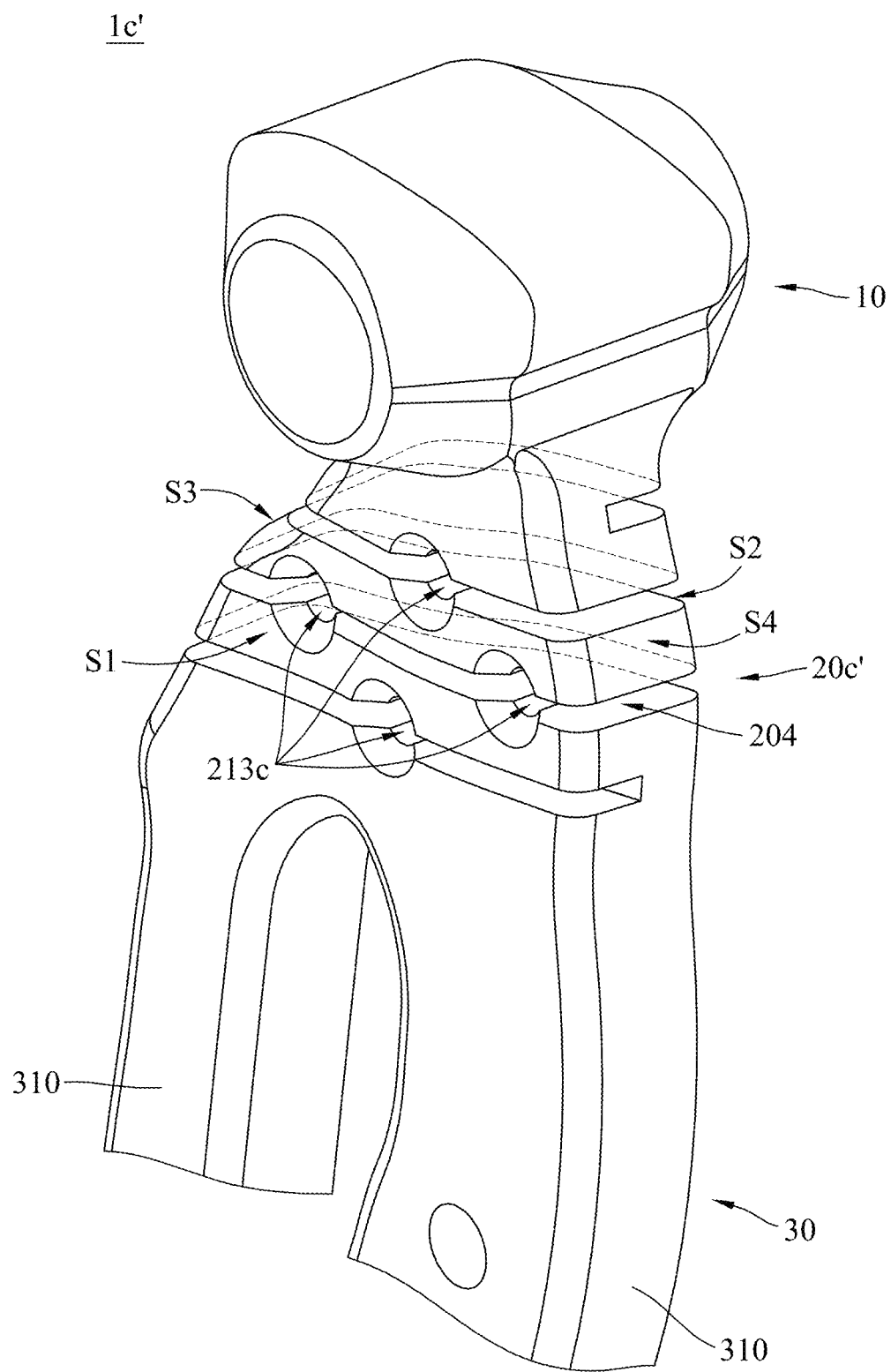
FIG. 7 illustrates a perspective view of a temporomandibular joint prosthesis according to another embodiment of the disclosure.

Alternatively, referring to FIG. 7, another embodiment of the disclosure provides a temporomandibular joint prosthesis 1c', as shown, having a configuration similar to that of the temporomandibular joint prosthesis 1c except for that a flexible unit 20c' of the temporomandibular joint prosthesis 1c' further has one or more adjustment holes 213c penetrating through the first surface S1 and the second surface S2. The adjustment holes 213b are for the insertion of suitable bone screw (not shown) so that the shape of the trench 204 can be adjusted by adjusting the insertion depth of the inserted bone screw, thereby adjusting the shape of the flexible unit 20c'. Other than that, the flexible unit 20c' also can enable complex three-dimensional motions of the fixation portion 30 and the joint portion 10 during the activities of lower jaw while serving as a cushion to effectively reduce or remove stress concentration on the boundaries among the temporomandibular joint prosthesis 1c', the mandible, and/or the cranial skeleton, thereby maintaining the jaw's functions and outward appearance and preventing pain, muscle tenderness, and uncomfortable sensation. For these reasons, the flexible unit 20c' also helps increase the durability and lifespan of the temporomandibular joint prosthesis 1c'.

Figure 8:
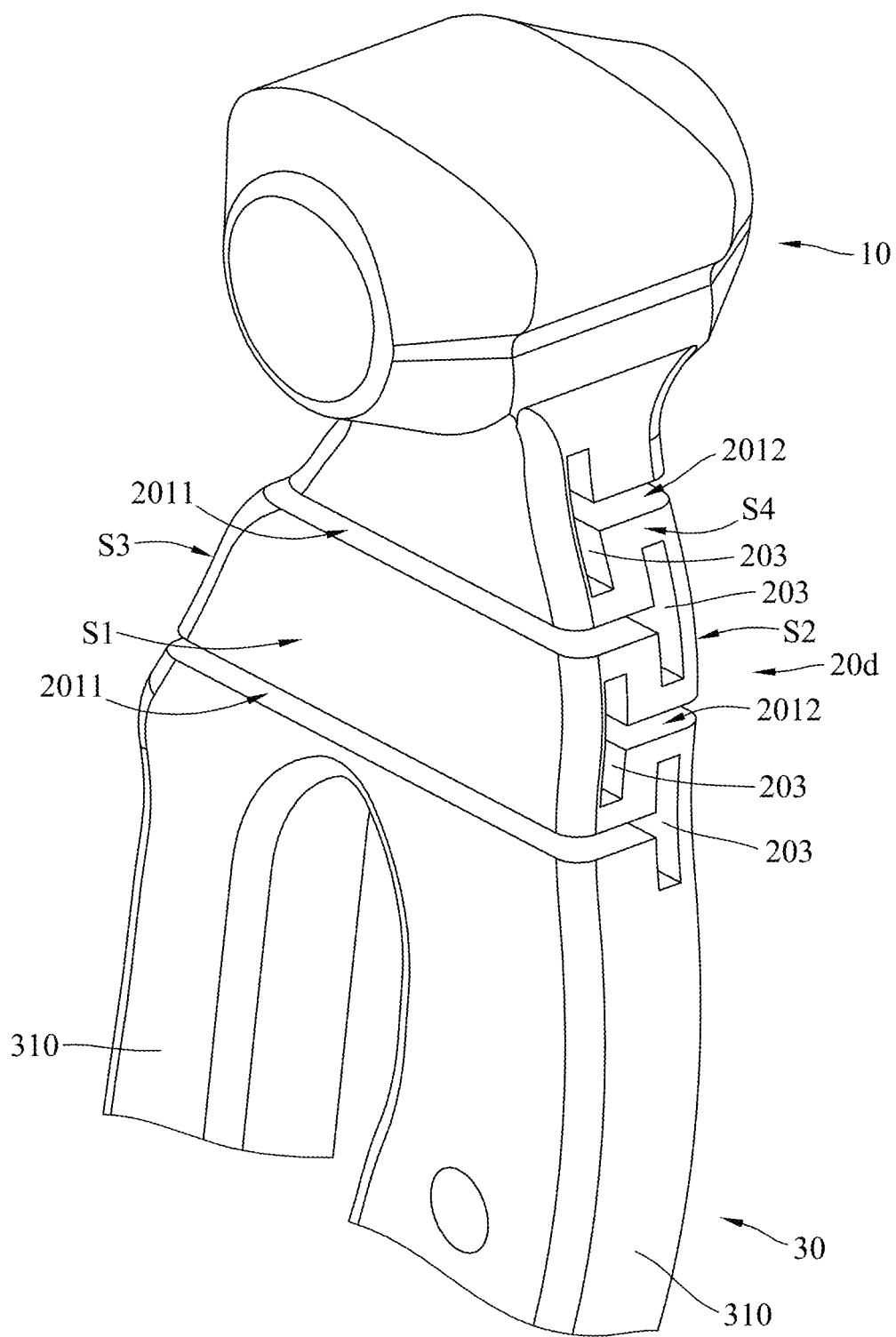
FIG. 8 illustrates a perspective view of a temporomandibular joint prosthesis according to another embodiment of the disclosure.

Alternatively, referring to FIG. 8, another embodiment of the disclosure provides a temporomandibular joint prosthesis 1d, as shown, having a configuration similar to that of the temporomandibular joint prosthesis 1a except for that a flexible unit 20d of the temporomandibular joint prosthesis 1d has no trenches 2021 and trenches 2022. The flexible unit 20d still can enable complex three-dimensional motions of the fixation portion 30 and the joint portion 10 during the activities of lower jaw while serving as a cushion to effectively reduce or remove stress concentration on the boundaries among the temporomandibular joint prosthesis 1d, the mandible, and/or the cranial skeleton, thereby maintaining the jaw's functions and outward appearance and preventing pain, muscle tenderness, and uncomfortable sensation. For these reasons, the flexible unit 20d also helps increase the durability and lifespan of the temporomandibular joint prosthesis 1d.

Figure 9:
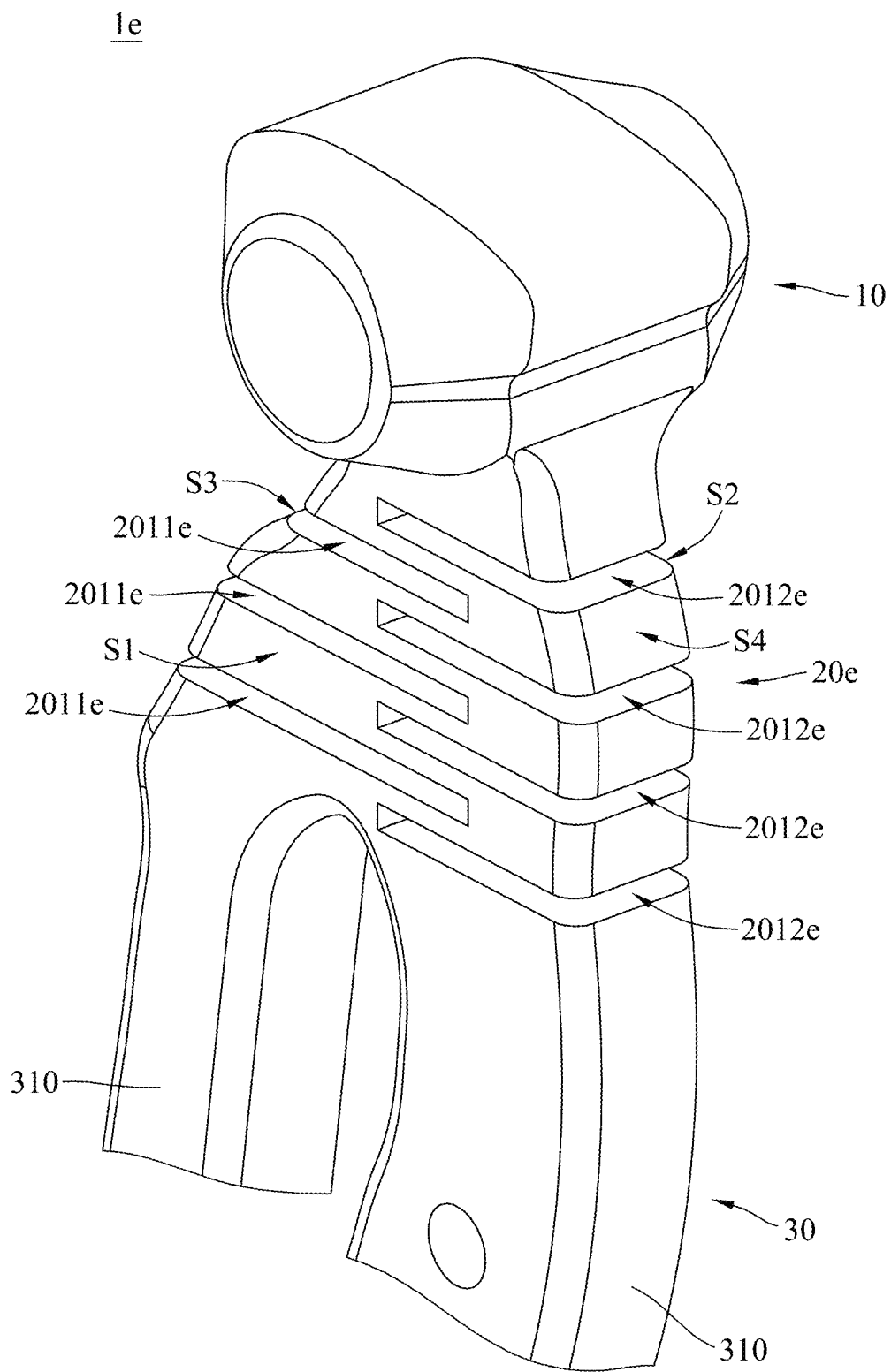
FIG. 9 illustrates a perspective view of a temporomandibular joint prosthesis according to another embodiment of the disclosure.

Alternatively, referring to FIG. 9, another embodiment of the disclosure provides a temporomandibular joint prosthesis 1e, as shown, having a configuration similar to that of the temporomandibular joint prosthesis 1b except for that a flexible unit 20e of the temporomandibular joint prosthesis 1e is in a serpentine shape of different shape and orientation compared to that of the flexible unit 20b. In specific, the flexible unit 20e has a plurality of first trenches 2011e (may simply be called 'trench 2011e' hereinafter) and a plurality of second trenches 2012e (may simply be called 'trench 2012e' hereinafter). The trenches 2011e penetrate through the first surface S1 and the second surface S2 and extend from the third surface S3 towards the fourth surface S4 but not yet reach or penetrate through the fourth surface S4. The trenches 2012e penetrate through the first surface S1 and the second surface S2 and extend from the fourth surface S4 towards the third surface S3 but not yet reach or penetrate through the third surface S3. The trenches 2011e and the trenches 2012e are arranged in a staggered manner. The flexible unit 20e also can enable complex three-dimensional motions of the fixation portion 30 and the joint portion 10 during the activities of lower jaw while serving as a cushion to effectively reduce or remove stress concentration on the boundaries among the temporomandibular joint prosthesis 1e, the mandible, and/or the cranial skeleton, thereby maintaining the jaw's functions and outward appearance and preventing pain, muscle tenderness, and uncomfortable sensation. For these reasons, the flexible unit 20e also helps increase the durability and lifespan of the temporomandibular joint prosthesis 1e.

Figure 10:
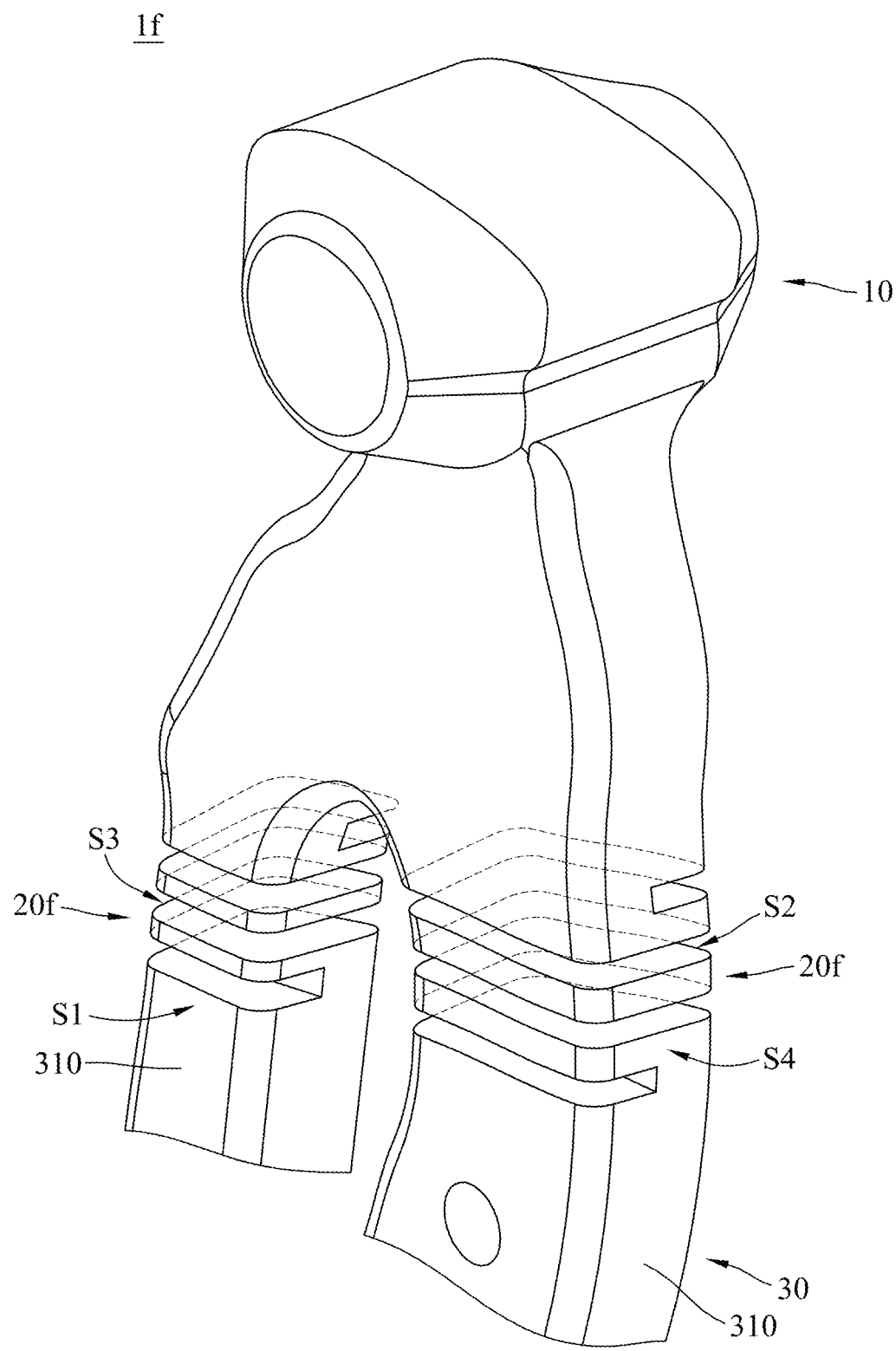
FIG. 10 illustrates a perspective view of a temporomandibular joint prosthesis according to another embodiment of the disclosure.

Alternatively, referring to FIG. 10, another embodiment of the disclosure provides a temporomandibular joint prosthesis 1f, as shown, having a configuration similar to that of the temporomandibular joint prosthesis 1d except for that the temporomandibular joint prosthesis if has two flexible units 20f each having a configuration similar to that of the flexible unit 20d. In specific, there are two flexible units 20f respectively for the two support portions 310 to connect the joint portion 10. The flexible unit 20f also can enable complex three-dimensional motions of the fixation portion 30 and the joint portion 10 during the activities of lower jaw while serving as a cushion to effectively reduce or remove stress concentration on the boundaries among the temporomandibular joint prosthesis 1f, the mandible, and/or the cranial skeleton, thereby maintaining the jaw's functions and outward appearance and preventing pain, muscle tenderness, and uncomfortable sensation. For these reasons, the flexible unit 20f also helps increase the durability and lifespan of the temporomandibular joint prosthesis 1f.

Figure 11:
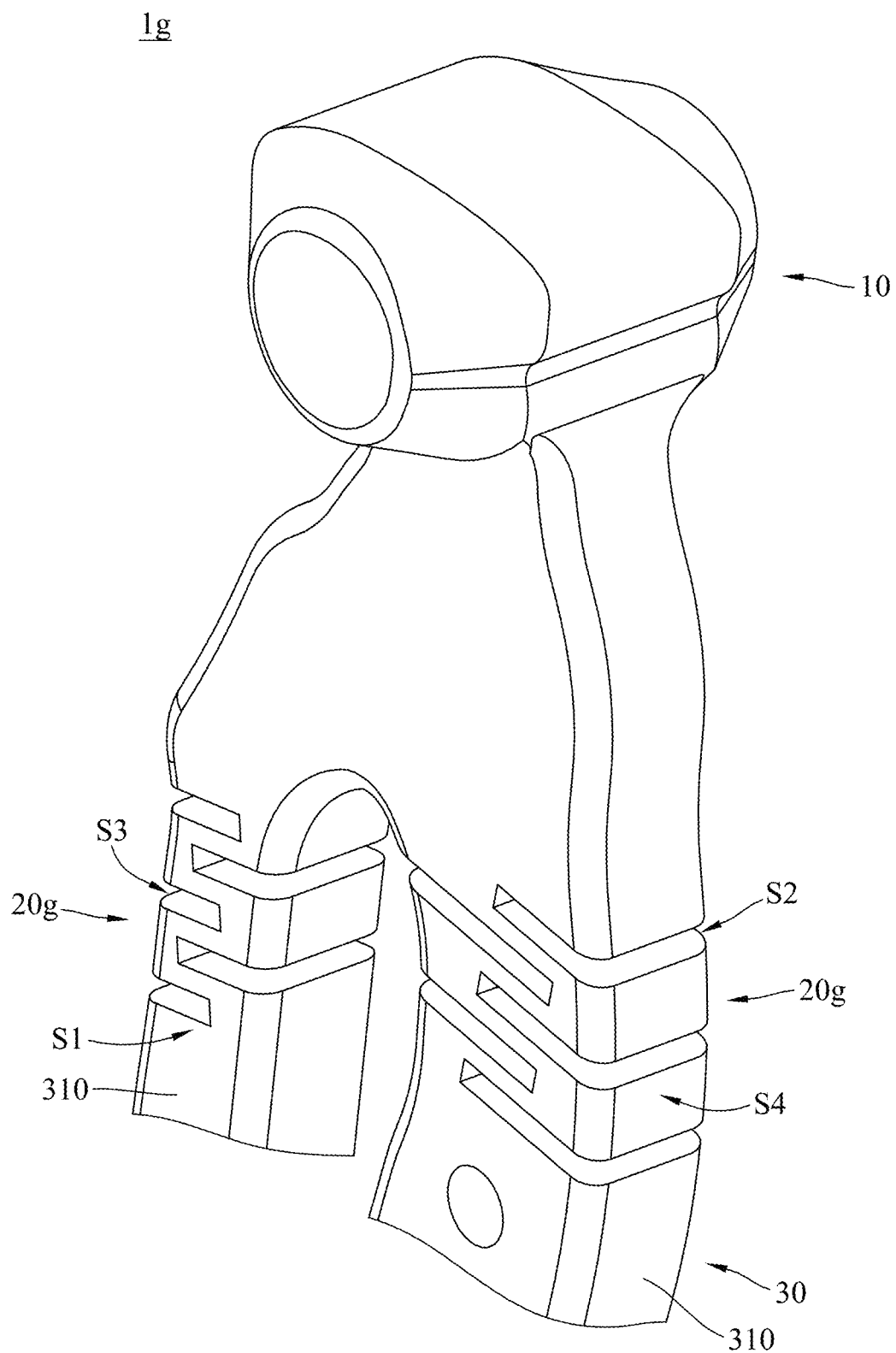
FIG. 11 illustrates a perspective view of a temporomandibular joint prosthesis according to another embodiment of the disclosure.

Alternatively, referring to FIG. 11, another embodiment of the disclosure provides a temporomandibular joint prosthesis 1g, as shown, having a configuration similar to that of the temporomandibular joint prosthesis 1e except for that the temporomandibular joint prosthesis 1g has two flexible units 20g each having a configuration similar to that of the flexible unit 20e. In specific, there are two flexible units 20g respectively for the two support portions 310 to connect the joint portion 10. The flexible unit 20g also can enable complex three-dimensional motions of the fixation portion 30 and the joint portion 10 during the activities of lower jaw while serving as a cushion to effectively reduce or remove stress concentration on the boundaries among the temporomandibular joint prosthesis 1g, the mandible, and/or the cranial skeleton, thereby maintaining the jaw's functions and outward appearance and preventing pain, muscle tenderness, and uncomfortable sensation. For these reasons, the flexible unit 20g also helps increase the durability and lifespan of the temporomandibular joint prosthesis 1g.

It should be noted that the disclosure is not limited by the above embodiments. As long as to enable the relative movement of the joint portion and the fixation portion while achieving a cushion thereto, one or more of the above flexible units are allowed to be incorporated into the same temporomandibular joint prosthesis.

According to the temporomandibular joint prosthesis as discussed in the above embodiments of the disclosure, during the various activities, such as speaking, chewing, and swallowing, the flexible unit connected between the joint portion and the fixation portion enables complex three-dimensional movements of the temporomandibular joint prosthesis and at the same time can be served as a cushion to reduce or remove stress concentration. As a result, the patient who used this temporomandibular joint prosthesis is free from pain, muscle tenderness, and uncomfortable sensation during the movement of lower jaw. In addition, the cushion provided by the flexible unit help increase the durability and lifespan of the temporomandibular joint prosthesis.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A temporomandibular joint prosthesis, comprising:
a joint portion, configured to be served as a temporomandibular joint and movably connected to cranial skeleton;
a fixation portion, configured to be fixed on mandible; and
at least one flexible unit, located between and connected to the joint portion and the fixation portion, wherein the fixation portion is movable with respect to the joint portion via the at least one flexible unit;
wherein the temporomandibular joint prosthesis has a first surface, a second surface, a third surface, and a fourth surface, the first surface and the second surface opposite to each other, the third surface and the fourth surface opposite to each other and located between the first surface and the second surface, the at least one flexible unit has a plurality of first trenches and a plurality of second trenches, the plurality of first trenches are spaced apart from one another and extend from the first surface towards the second surface but do not penetrate through the second surface, the plurality of second trenches are spaced apart from one another and extend from the second surface towards the first surface but do not penetrate through the first surface.

2. The temporomandibular joint prosthesis according to claim 1, wherein the plurality of first trenches and the plurality of second trenches extend from the third surface to the fourth surface, and the plurality of first trenches and the plurality of second trenches are arranged in a staggered manner viewing from the third surface.

3. The temporomandibular joint prosthesis according to claim 1, wherein each of the plurality of first trenches is tapered towards the second surface, and each of the plurality of second trenches is tapered towards the first surface.

4. The temporomandibular joint prosthesis according to claim 1, wherein the at least one flexible unit further has a plurality of third trenches, a plurality of fourth trenches, and a plurality of fifth trenches, the plurality of third trenches are located at the first surface and extend from one of the first trenches to another one of the first trenches, the plurality of fourth trenches are located at the second surface and extend from one of the second trenches to another one of the second trenches, the plurality of fifth trenches extend from the third surface to the fourth surface, a part of the plurality of fifth trenches are spaced apart from each other and respectively directly connect ends of the second trenches and the plurality of third trenches, another part of the plurality of fifth trenches are spaced apart from each other and respectively directly connect ends of the first trenches and the plurality of fourth trenches.

5. The temporomandibular joint prosthesis according to claim 4, wherein the plurality of first trenches and the plurality of third trenches are orthogonal to each other, and the plurality of second trenches and the plurality of fourth trenches are orthogonal to each other.

6. The temporomandibular joint prosthesis according to claim 1, wherein the at least one flexible unit further has at least one adjustment hole located at the first surface and overlapping with at least one of the first trenches, the at least one adjustment hole is for an insertion of a bone screw.

* * * * *